Figure 1A:
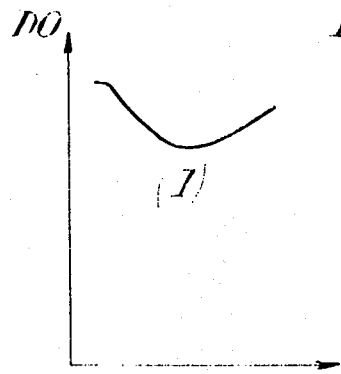

United States Patent [19]

Raby et al.

[11] 3,968,215
[45] July 6, 1976

[54] DRUG HAVING AN ANTI-AGGLUTINATING EFFECT ON PLATELETS AND HYPOCOAGULATING EFFECT

[75] Inventors: Claude Raby, Chaville; Jean Choay, Paris, both of France

[73] Assignee: Choay S.A., Paris Cedex, France

[22] Filed: Aug. 27, 1974

[21] Appl. No.: 500,888

[30] Foreign Application Priority Data
Aug. 31, 1973 France .............................. 73.31668

[52] U.S. Cl. .............................................. 424/260
[51] Int. Cl.² ....................................... A61K 31/485
[58] Field of Search .................................. 424/260

[56] References Cited
OTHER PUBLICATIONS
Chem. Abst. vol. 65 – 14289–G (1966).
The Merck Index, 7th Ed. (1960), p. 695.

*Primary Examiner*—Stanley J. Friedman
*Attorney, Agent, or Firm*—Weiser, Stapler & Spivak

[57] ABSTRACT

A drug having an anti-agglutinating effect on platelets and a hypocoagulating effect formed of an association of papaverine or a physiologically acceptable salt thereof with a thiosulphate of a physiologically acceptable metal.

21 Claims, 5 Drawing Figures

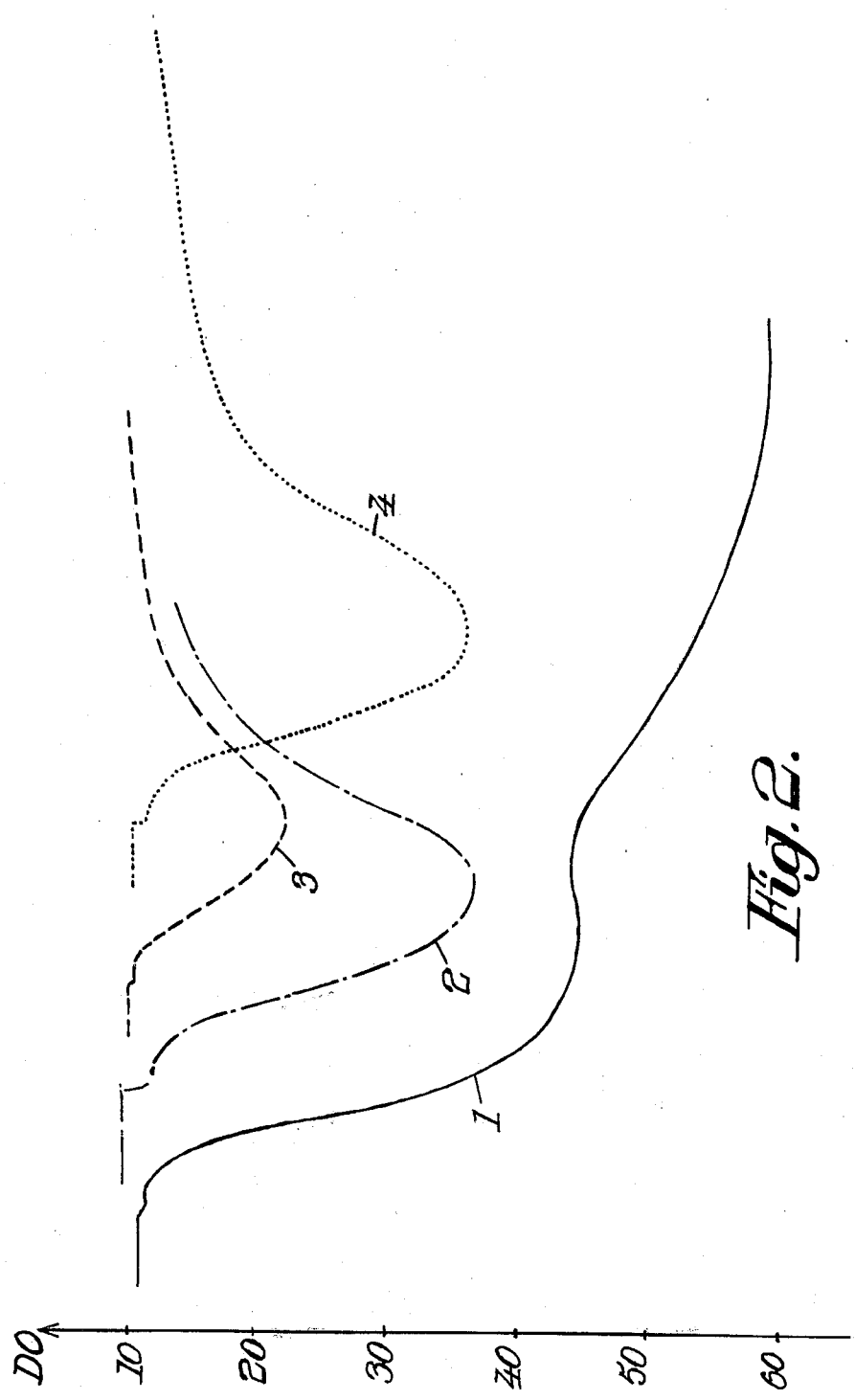

DRUG HAVING AN ANTI-AGGLUTINATING EFFECT ON PLATELETS AND HYPOCOAGULATING EFFECT

The invention relates to a novel drug which prevents blood platelets from agglutinating and also has a hypocoagulating action.

It is generally agreed that the tendency to hyperagglutination of the blood platelets is the cause of a number of mainly arterial thromboses. Of course, other inducing agents can be regarded as the main substances responsible for certain thromboses. Even in such cases, however, the harmful effect of these inducing agents will be accentuated by a tendency to hyperadhesion and hyperagglutination of blood platelets.

Certain known drugs, hereinafter called platelet anti-agglutinating drugs, are in many cases adapted to cure the tendency to hyperadhesion and hyperagglutination of platelets. It is known, however, that these disturbances usually have a more or less long-term effect on other factors in the coagulating system and inter alia tend to increase the tendency to coagulate in these patients.

Known anti-platelet drugs, however, have practically no effect on plasma coagulation, and it has therefore been proposed to associate the platelet anti-agglutinating drugs in treatment with anti-coagulant drugs such as heparin and anti-vitamin K. Noteworthy results can be obtained when the anti-coagulant used is heparin. The latter drug has an excellent curative effect but its use is inconvenient in practice, more particularly in prolonged treatment, in view of the fact that there are no known heparin-based drugs which can be administered by other than parenteral means.

In general, much less satisfactory results are obtained by treatment with orally administered platelet anti-agglutinating drugs in association with orally administered anti-vitamin K products. Anti-vitamin K products have no direct effect on the thrombogenic factors and merely have a palliative effect which is often difficult to check.

An object of the invention, therefore, is to obtain a platelet anti-agglutinating drug which has a wider and completely controllable range of action and which is also active when orally or rectally administered.

The drug according to the invention is characterised by an association of papaverine or a physiologically acceptable salt thereof with a thiosulphate of a physiologically acceptable metal.

The association according to the invention has an inhibiting effect on hyperadhesion and hyperagglutination between platelets and simultaneously has a marked hypocoagulating effect on the kinetic and dynamic coagulability of whole blood.

It is found that the thiosulphate-papaverine association considerably potentiates the anti-agglutinating effect of papaverine.

In preferred embodiments of the drug according to the invention, papaverine hydrochloride, citrate or thienyl 2-carboxylate is associated with magnesium thiosulphate.

The hypocoagulating effect of the association is noteworthy in that it acts simultaneously on the kinetic and dynamic coagulability, whereas thiosulphate alone, inter alia magnesium thiosulphate, acts only on the kinetic coagulability and papaverine has never been considered to have hypocoagulating properties, even though pharmacological tests in vitro (to be described hereinafter) show that it has a slight effect on the dynamic coagulability of blood plasma. It is found that papaverine by itself actually tends to have a contrary effect on kinetic coagulability.

Since the drug according to the invention has combined hypocoagulating and platelet anti-agglutinating effects, it has a wide range of applications in therapy. The importance of the drug according to the invention is increased by the fact that it can be orally administered. The constituents of the association cross the digestive barrier without adverse effect.

The drug according to the invention can be used for treating all morbid conditions simultaneously involving a tendency to platelet hyperagglutination and to hypercoagulability. Such conditions are inter alia vascular accidents and peripheral, more particularly cerebral vascular accidents.

Since the constituents are well known to be harmless, they can be used for both long-term and preventive treatment. The drug is preferably used for improving the cerebral circulation and the microcirculation in general. It prevents obstruction of vessels by clumps of platelets, owing to its anti-agglutinating effect, and increases the fluidity of blood in circulation, inter alia because of its hypocoagulating action.

The association according to the invention may also advantageously be used for preventing complications in hyperlipidemia, certain forms of diabetes and atheroma, such complications being particularly frequent in persons subject to hyper-agglutination of platelets.

The drug according to the invention may also particularly advantageously be used as a temporary substitute for heparin in patients who, owing to an excessive tendency to hypercoagulability, are given prolonged treatment with heparin. Hitherto, it has been impossible to interrupt such treatment without risking a rapid deterioration in the results obtained, inter alia a return to hypercoagulability exposing the patients to multiple risks of thrombo-embolisms, mainly in the heart, brain or lower limbs or in the microcirculation regions (kidneys, lungs and retina). In these cases, however, it is found that the associating according to the invention can prolong the beneficial effect of heparin, inter alia by reducing the tendency to coagulate. Accordingly the drug according to the invention, which is orally administered, can be used for maintenance treatments which bring considerable relief to the patients, even though they are only temporary and do not obviate the need for temporary treatment with heparin.

In general, the drug according to the invention is of use in both human and veterinary medicine.

Figure 1B:
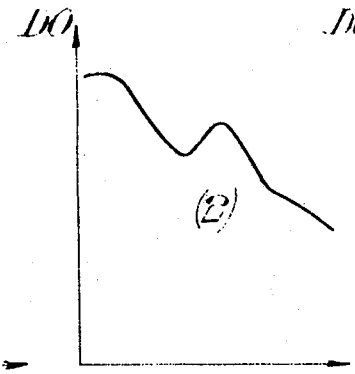
Figure 1C:
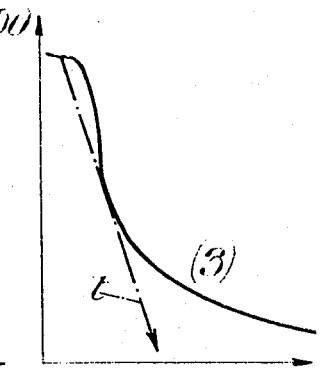

Other features of the invention will be clear from the following description of pharmacological tests showing the aforementioned properties. Parts of the description refer to the accompanying graphs, in which:

FIGS. 1a, 1b, 1c show three curves representing three kinds of agglutination processes which may be observed in blood plasma rich in platelets (P.R.P.), the curbes being obtained by turbidimetry (graphic recording of variations with time in the optical density of the medium).

Figure 3:
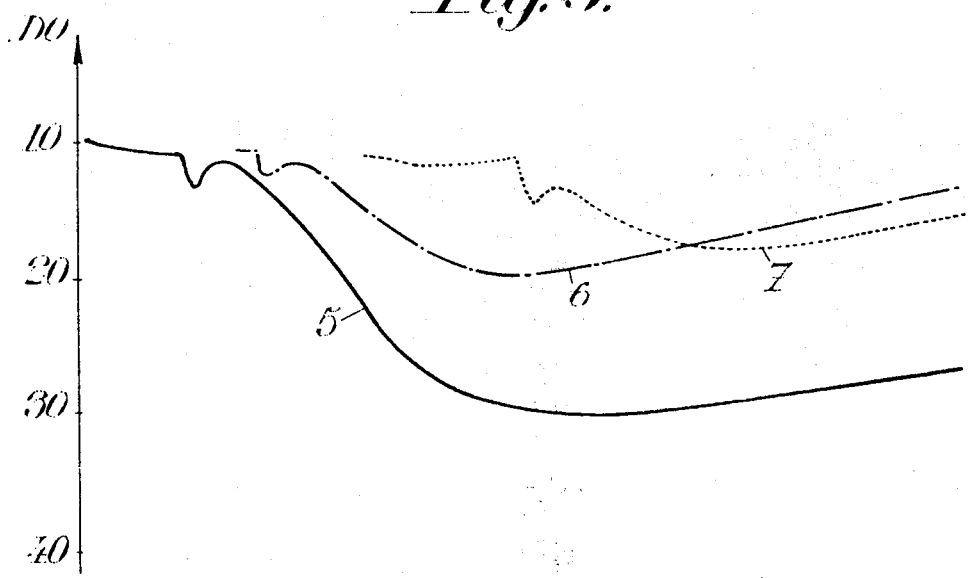

FIGS. 2 and 3 show curves representing the same phenomena, inter alia for the purpose of illustrating the anti-agglutinating effect of given doses of (a) magnesium thiosulphate, (b) papaverine hydrochloride and (c) associations of magnesium thiosulphate and papaverine hydrochloride on normal (FIG. 2) and pathological (FIGS. 3) plasmas in contact with a conventional agent for inducing platelet agglutination, inter alia adenosine diphosphate (ADP).

A. Action on agglutination of platelets

1. Action of the association of papaverine hydrochloride with magnesium thiosulphate The pharmacological tests, the results of which are given hereinafter, are based on the following principle. The antagonistic action of the anti-agglutinating agents under study are tested by turbidimetry in a plasma rich in platelets to which an agglutinating agent such as ADP is added.

A plasma rich in platelets is opaque if agglutinating agents have not been added. Increasing quantities of ADP, when added to the plasma, induce the processes diagrammatically shown in FIGS. 1a, 1b and 1c. If ADP is added to a plasma rich in platelets and in the non-agglutinated state, it induces agglutination of the platelets. If the quantity of ADP used is insufficient, agglutination does not continue and the medium tends to return to its previous state of disintegration. We then have the phenomenon which is called "agglutination and disintegration.". When this phenomenon is observed by turbidimetry, a decrease is observed in the optical density of the medium, followed by the reverse phenomenon. All these phenomena are represented by the curve in FIG. 1a (type 1 curve). This curve tends to become hollower when an increased amount of ADP is added to the plasma rich in platelets. When the quantity of ADP is increased, the resulting agglutination is followed by a temporary disintegration phase, after which agglutination continues (secondary agglutination) as a result of the ADP liberated by the platelets themselves (which is called the "release" phenomenon). The last-mentioned process is represented by the curve in FIG. 1b, hereinafter called "type 2 curve."

If still larger quantities of ADP are added to the medium, the result is a massive agglutination, shown by a rapid decrease in the optical density of the medium. The curve in FIG. 1c, called a "type 3 curve," represents the aforementioned massive agglutination. The intensity of the agglutination process is inversely proportional to the angle between the coordinate axis and the straight line $t$, which is a tangent to the curve and which passes through the point on the curve corresponding to zero time (the instant when ADP is introduced into the medium) that is, the smaller the angle, the more intense the agglutination. Massive agglutination of the aforementioned kind is observed more particularly when a quantity of ADP corresponding to an ADP concentration of $2.10^{-9}$ mols/ml of platelet suspension is added to a normal plasma rich in platelets.

The activity of an anti-agglutinating agent can be estimated from the modifications which it produces in the agglutination curves induced by adding a given quantity of ADP to a given quantity of plasma rich in platelets. If, in the presence of the agent under test, a given quantity of ADP induces only a type 2 or even a type 1 curve, whereas the absence of the agent under test, the same quantity of ADP produces massive agglutination, we can conclude that the agent under test has anti-agglutinating properties.

a. Tests with a normal plasma

In the following tests, use was made of the following solutions (in an isotonic medium buffered to pH 7.35):

| Solution A- | Mg thiosulphate | 20 mg/ml |
|---|---|---|
| Solution B- | Papaverine hydrochloride | 2 mg/ml |
| Solution C - | (Mg thiosulphate | 20 mg/ml |
|  | (Papaverine hydrochloride | 2 mg/ml |

The tests were made on a volume of 250 $\mu$l comprising:
- 230 $\mu$l of P.R.P. containing 250,000 to 300,000 platelets per mm$^3$ and
- 20 $\mu$l of the solution of the product under test (or of the buffer solution in the case of the controls).

The concentration of the products under test is expressed as the final concentration per ml of platelet suspension (P.R.P. + solution of product under test).

The tests were made under the following conditions: The 20 $\mu$l of buffer solution or of dilute solution of anti-agglutinating agent under test were added to the 230 $\mu$l of a suspension of platelets in the cell of a turbidimeter (a photometer provided with a magnetic agitator). The medium was incubated at 37°C for 5 minutes without agitation. The agitator was started and kept in operation from 1½ minutes. Next, the ADP was added ($2.10^{-9}$ mols/ml of P.R.P.). Variations with time in the optical density were graphically recorded, the optical density decreasing during agglutination and increasing during disintegration of platelets.

As can be seen, magnesium thiosulphate does not have an anti-agglutinating effect except at relatively high doses. At doses above 300 $\mu$g/ml of magnesium thiosulphate, the curves showing the variation in optical density are type 1 (agglutination-disintegration). At doses between 320 and 100 $\mu$g/ml magnesium thiosulphate, type 2 curves are obtained (secondary agglutination). At a dose of 106.6 $\mu$g/ml, a transition curve (curve 1 in FIG. 2) between a type 2 curve and a type 3 curve is observed.

Papaverine is more active than magnesium thiosulphate. At doses of papavarine hydrochloride above 10 $\mu$g/ml P.R.P., type 1 agglutination-disintegration curves are obtained. In the presence of 10 $\mu$g of papaverine hydrochloride per ml of P.R.P., we obtain a curve which marks a transition between a type 1 curve and a type 2 curve. Curve 2 in FIG. 2 was obtained with a final concentration of 10.66 $\mu$g papaverine hydrochloride per ml of P.R.P., under the conditions given hereinbefore.

The mixture of magnesium thiosulphate and papaverine hydrochloride considerably potentiates the action of the latter substance, as shown by the type 1 curve 3 in FIG. 2, which was obtained with an association of 106.6 $\mu$g magnesium thiosulphate and 10.66 $\mu$g of papaverine hydrochloride per ml P.R.P., and the type 1 curve 4 in FIG. 2, obtained with an association of 64 $\mu$g magnesium thiosulphate and 6.4 $\mu$g papaverine hydrochloride.

A comparison between curves 2 and 4 shows that the association of 6.4 $\mu$g papaverine and 64. $\mu$g magnesium thiosulphate has a greater anti-agglutinating effect than is obtained with 10.66 $\mu$g of papaverine hydrochloride per ml P.R.P.

At the aforementioned relative basis, magnesium thiosulphate, which is a weak anti-agglutinating agent, doubles the activity of the corresponding dose of papaverine when used alone. Note also that the association of the two products potentiates the action of papaverine so that a given anti-agglutinating effect can be obtained with half the dose of the latter substance. The action can also be increased if the more constituent is maintained at a constant concentration.

b. Tests on pathological plasma

The plasma used in this test was a pathological plasma containing platelets which showed hyperagglutination. In the control preparations, a type 2 curve was obtained with an ADP concentration of $0.5 \cdot 10^{-9}$ mol/ml of platelet suspension (a quantity of inducing agent which has no effect on normal platelets).

In the tests described hereinafter, the same method was used as in the previous case, except that the platelet suspension contained approx. 380,000 platelets per $mm^3$ P.R.P.

When 320 μg (the final concentration) of magnesium thiosulphate was added to this system, the result was only a reduction in the agglutination kinetics and the curve was still type 3 (curve 5 in FIG. 3).

The introduction of 16 μg (the final concentration) of papaverine hydrochloride by itself resulted in agglutination and partial disintegration (curve 6). When, however, the 16 μg of papaverine hydrochloride was associated with 160 μg of magnesium thiosulphate (i.e. a quantity twice as small as the previously-mentioned quantity) there was a very considerable increase in the effect of the aforementioned quantity (16 μg) of papaverine hydrochloride (curve 7). The effect was practically the same as that obtained with a double dose of papaverine hydrochloride.

2. The action of another papaverine salt in association with magnesium thiosulphate In experiments made under conditions similar to those described above, it was found that the anti-agglutinating effects of papaverine thienyl 2-carboxylate and papaverine citrate were greatly potentiated by magnesium thiosulphate, more particularly for concentrations of magnesium thiosulphate which were not active by themselves. This potentiating effect was observed at concentrations of 150 μg of magnesium thiosulphate per ml of P.R.P. The potentiation relates inter alia to the disintegration kinetics.

More particularly, there was a considerable reduction in the agglutination of platelets under the aforementioned experimental conditions, even in the presence of massive quantities of ATP, produced by an association of papaverine thienyl 2-carboxylate and magnesium thiosulphate at concentrations of 25 μg and 250 μg respectively per ml of P.R.P.

The preceding tests show the remakable effects of an association of compounds such as papaverine and magnesium thiosulphate.

B. Hypocoagulating properties of the association according to the invention

TESTS IN VITRO

In order to illustrate the following description, we recall that the coagulation of blood is normally started by the activation of certain factors in contact with normally hydrophobic vascular endothelia which become hydrophilic as a result of mechanical or other lesions. The first stage in the coagulation process, called the thromboplastinoformation stage (formation of prothombinase) is induced by the interaction of plasmatic and blood cellular factors in the presence of calcium ions.

The hypocoagulating properties of magnesium thiosulphate, papaverine-hydrochloride and an association of the aforementioned two constituents was studied by the thromboelastography method on preparations (in tubes the walls of which are coated with a water imperious inter alia a silicone, layer) of plasmas rich in platelets in which the calcium ions were chelated by citrate ions. Under these conditions, the contact factors in the preparations are activated to a minimum extent and the preparations do not coagulate (absence of ionized calcium); the coagulation process can be started by re-calcification, by adding calcium chloride in suitable proportions.

The products under test were used in the form of a solution in an isotonic aqueous medium buffered to pH 7.35.

In the case of papaverine thienyl 2-carboxylate, one tenth of the aqueous medium was replaced by methanol. Preliminary experiments showed that methanol, when diluted to 1/6 or more did not have any effect on total coagulability.

The solutions had the following compositions:

| | |
|---|---|
| Mg thiosulphate | 10 mg/ml |
| Papaverine hydrochloride | 1 mg/ml |
| Mixture (Mg thiosulphate) | 10 mg/ml |
| (Papaverine hydrochloride) | 1 mg/ml |
| Papaverine citrate | 1.41 mg/ml |
| Mixture (Mg thiosulphate) | 10 mg/ml |
| (Papaverine citrate) | 1.41 mg/ml |
| Papaverine thienyl 2-carboxylate | 1.24 mg/ml |
| Mixture (magnesium thiosulphate) | 10 mg/ml |
| (papaverine thienyl 2-carboxylate) | 1.24 mg/ml |

The solutions under test were added to the plasma rich in platelets (P.R.P.) in the proportion of 0.1 ml of solution per ml of P.R.P.

Basically, the method consisted in comparing the plasma coagulation time between the different preparations and control preparations having the same composition but not containing a hypocoagulant, using the method described in "Biologie des Hemorragies et des Thromboses," C. Raby – Masson Ed. Paris 1966 (pp. 186 – 188).

This method takes advantage of the increase in viscosity of a blood preparation during the coagulation process. Basically the method consists in causing the cell containing the preparation under study to oscillate through an angle and studying the effects of coagulation on a cylinder suspended at the end of a torsion wire and immersed in the preparation. When coagulation begins, the plasma in the cell drives the cylinder during its oscillatory motion.

The coagulation instant $t = 0$ is taken as the instant when the factors responsible for coagulation are activated by adding $Ca^{++}$ ions under the aforementioned conditions.

The following terms are used:
$r$ = the latency time before the actual beginning of coagulation;
$a\ m$ = the maximum amplitude of the cylinder oscillations;
$k$ = the time interval between the instant when the cylinder begins to oscillate and the instant when the amplitude of motion thereof becomes equal to the maximum amplitude (20 mm) obtained under the same conditions using a plasma not containing platelets and having a normal fibrinogen content (0.3 to 0.4 G/%).

The "total coagulation time" of a preparation is given the sum $r + k$.

The coagulation kinetics is expressed by the parameters $r$ and $r+k$ and the coagulation dynamics is expressed by the maximum amplitude am of the cylinder oscillation.

We shall now give the results measured in a test series, each test being performed on:

a. normal plasma (1 ml) in the presence of the buffer substance (0.1 ml) (control);

b. the same plasma (1 ml) in the presence of 0.1 ml of a solution of 10 mg magnesium thiosulphate per ml;

c. the same plasma (1 ml) in the presence of 0.1 ml of a solution of 1 mg papaverine-hydrochloride per ml;

d. the same plasma (1 ml) in the presence of a mixture of 0.1 ml of a solution containing 10 mg magnesium thiosulphate and 1 mg papaverine hydrochloride per ml;

e. the same plasma (1 ml) in the presence of 0.1 ml of the aforementioned solution of papaverine citrate;

f. the same plasma (1 ml) in the presence of 0.1 ml of the aforementioned solution of a mixture of magnesium thiosulphate and papaverine citrate;

g. the same plasma (1 ml) in the presence of 0.1 ml of the aforementioned solution of papaverine thienyl 2-carboxylate; and h. the same plasma (1 ml) in the aforementioned solution of the aforementioned mixture of magnesium thiosulphate and papaverine thienyl 2-carboxylate.

i. Tests involving magnesium thiosulphate and papaverine hydrochloride.

Test No. 1

|     | r  | k  | r + k | a m  |
|-----|----|----|-------|------|
| (a) | 26 | 16 | 42    | 61   |
| (b) | 39 | 14 | 53    | 61   |
| (c) | 26 | 15 | 41    | 53   |
| (d) | 56 | 51 | 107   | <35  |

Test No. 2

|     | r  | k  | r + k | a m |
|-----|----|----|-------|-----|
| (a) | 34 | 18 | 52    | 54  |
| (b) | 41 | 18 | 59    | 62  |
| (c) | 27 | 12 | 39    | 40  |
| (d) | 65 | not measurable | | 13 |

Test No. 3

|     | r  | k  | r + k | a m |
|-----|----|----|-------|-----|
| (a) | 32 | 9  | 41    | 54  |
| (b) | 42 | 27 | 69    | 55  |
| (c) | 28 | 21 | 49    | 34  |
| (d) | 49 | 64 | 113   | 24  |

Test No. 4

|     | r  | k  | r + k | a m |
|-----|----|----|-------|-----|
| (a) | 30 | 15 | 45    | 55  |
| (b) | 31 | 28 | 59    | 56  |
| (c) | 28 | 10 | 38    | 57  |
| (d) | 43 | 36 | 79    | 28  |

Test No. 5

|     | r  | k  | r + k | a m |
|-----|----|----|-------|-----|
| (a) | 24 | 17 | 41    | 59  |
| (b) | 37 | 17 | 54    | 60  |
| (c) | 27 | 25 | 52    | 31  |
| (d) | 48 | not measurable | | 16 |

The tables hereinbefore show that magnesium thiosulphate has a slight effect on the parameter $r$ and an inconsistent effect on the parameter K. In other words, it has a slight effect on kinetic coagulability but has no effect on $a\ m$, i.e. on dynamic coagulability (except in test No. 2 where it actually tends to increase it).

Papaverine hydrochloride does not increase the time $r$ but actually tends to decrease it. It has a slight effect on dynamic coagulability.

The results of tests 1 to 5, however, show the marked hypocoagulating effects of an association of magnesium thiosulphate and papaverine hydrochloride on both the kinetic and the dynamic coagulability. The association has the novel feature of being a mixed hypocoagulant, since it reduces both kinetic and dynamic coagulability.

The aforementioned results were confirmed in tests made with larger concentrations of magnesium thiosulphate and papaverine hydrochloride. Blood plasma incapable of coagulation were rapidly obtained.

2. Tests involving magnesium thiosulphate and papaverine citrate

Test No. 1

|     | r  | k  | r + k | a m |
|-----|----|----|-------|-----|
| (a) | 19 | 11 | 30    | 56  |
| (e) | 43 | —  | —     | 10  |

Test No. 2

|     | r  | k  | r + k | a m |
|-----|----|----|-------|-----|
| (a) | 37 | 19 | 56    | 57  |
| (e) | 71 | —  | —     | 13  |

Test No. 3

|     | r  | k  | r + k | a m |
|-----|----|----|-------|-----|
| (a) | 30 | 12 | 42    | 55  |
| (b) | 51 | 20 | 71    | 56  |
| (e) | 45 | 38 | 83    | 27  |

Test No. 4

|     | r  | k  | r + k | a m |
|-----|----|----|-------|-----|
| (a) | 28 | 17 | 45    | 55  |
| (b) | 31 | 18 | 49    | 53  |
| (e) | 64 | 60 | 124   | 21  |

Test No. 5

|     | r  | k  | r + k | a m |
|-----|----|----|-------|-----|
| (a) | 29 | 10 | 39    | 44  |
| (b) | 58 | 28 | 86    | 52  |
| (c) | 70 | —  | —     | —   |

Test No. 6

|     | r  | k  | r + k | a m |
|-----|----|----|-------|-----|
| (a) | 31 | 19 | 50    | 54  |
| (f) | 49 | 46 | 95    | 28  |

Test No. 7

|     | r  | k  | r + k | a m |
|-----|----|----|-------|-----|
| (a) | 37 | 17 | 54    | 42  |
| (f) | 47 | 58 | 105   | 21  |

Test No. 8

|     | r  | k  | r + k | a m |
|-----|----|----|-------|-----|
| (a) | 23 | 10 | 33    | 54  |
| (f) | 58 | 44 | 102   | 26  |

The conclusions which can be drawn from the last-mentioned results are similar to those drawn in the case of an association of magnesium thiosulphate and papaverine citrate.

3. Tests involving magnesium thiosulphate and papaverine thienyl 2-carboxylate

Test No. 1

|     | r  | k  | r + k | a m |
|-----|----|----|-------|-----|
| (a) | 33 | 18 | 51    | 56  |
| (g) | 42 | —  | —     | 19  |

Test No. 2

|     | r  | k  | r + k | a m |
|-----|----|----|-------|-----|
| (a) | 28 | 11 | 39    | 53  |
| (g) | 44 | 25 | 69    | 38  |

Test No. 3

|     | r  | k  | r + k | a m |
|-----|----|----|-------|-----|
| (a) | 28 | 13 | 41    | 55  |
| (h) | 43 | 97 | 140   | 20  |

Test No. 4

|     | r  | k  | r + k | a m |
|-----|----|----|-------|-----|
| (a) | 18 | 5  | 23    | 69  |
| (h) | 35 | 20 | 55    | 32  |

Test No. 5

|     | r  | k  | r + k | a m |
|-----|----|----|-------|-----|
| (a) | 23 | 7  | 30    | 70  |
| (h) | 31 | 23 | 54    | 31  |

These results show that papaverine thienyl 2-carboxylate has a moderate effect on kinetic coagulability and simultaneously has a somewhat more marked effect on dynamic coagulability. An association of the aforementioned papaverine salt with magnesium thiosulphate has a remarkable effect both on kinetic and on dynamic coagulability.

TESTS IN VIVO

Rabbits (weighing approx. 3 kilograms) were forcibly fed twice a day with 5 ml of a solution containing 25 mg magnesium thiosulphate and 2.5 mg papaverine hydrochloride per ml. Thromboelastographic measurements were made on (a) the whole blood and (b) the plasma rich in platelets of the rabbits, at the times given in the following table.

The table gives the values of $r$, $k$, $r + k$ and $a\,m$, and also gives the results of measurements of the thrombodynamic potential index (IPT) made on the whole blood, the index being given by the ratio $Emx$ where $$Emx = \frac{100\,a\,m}{100 - a\,m}$$

and used to quantify the dynamic coagulability.

| Rabbit No. 999 | r | k | r+k | a m | IPT |
|---|---|---|---|---|---|
| Before forced feeding | | | | | |
| 1. Whole blood | 9 | 5 | 14 | 64 | 35 |
| 2. P.R.P. | 14 | 6 | 20 | 72 | |
| After forced feeding | | | | | |
| (2 hours after 3rd forced feed) | | | | | |
| 1. Whole blood | 21 | 9 | 30 | 66 | 21 |
| 2. P.R.P. | 94 | 47 | 141 | 53 | |
| Rabbit No. 804 | | | | | |
| Before forced feeding | | | | | |
| 1. Whole blood | 17 | 8 | 25 | 69 | 27 |
| 2. P.R.P. | 41 | 34 | 75 | 67 | |
| After forced feeding | | | | | |
| (2 hours after 7th forced feed) | | | | | |
| 1. Whole blood | 21 | 9 | 30 | 67 | 22 |
| 2. P.R.P. | 83 | 36 | 119 | 65 | |
| Rabbit No. 805 | | | | | |
| Before forced feeding | | | | | |
| 1. Whole blood | 9 | 6 | 15 | 60 | 25 |
| 2. P.R.P. | 15 | 10 | 25 | 72 | |
| After forced feeding | | | | | |
| (2 hours after 7th forced feed) | | | | | |
| 1. Whole blood | 43 | 16 | 59 | 49 | 6 |
| 2. P.R.P. | 75 | 77 | 152 | — | |
| (7 hours after 7th forced feed) | | | | | |
| 1. Whole blood | 25 | 12 | 37 | 56 | 10 |
| 2. P.R.P. | 140 | 68 | 208 | 58 | |

The results given in the table hereinbefore show that the association is absorbed orally and that, at the ingested doses, kinetic hypocoagulability appears approx. 1½ hours after the first forced feed and persists at least 7 hours after the last feed.

The results given in the table hereinbefore show that the association is absorbed orally and that, at the ingested doses, kinetic hypocoagulability appears approx. 1½ hours after the first forced feed and persists at least 7 hours after the last feed.

Similar though less marked results are obtained with associations of papaverine hydrochloride and sodium thiosulphate. Similar results are also obtained with papaverine citrate which, as is known, has approximately the same action as that of papaverine hydrochloride on the agglutination between platelets. Sodium thiosulphate by itself has a positive hypocoagulant effect on the kinetic coagulability only (the effect being less than that of magnesium thiosulphate). However, associations of sodium thiosulphate and papaverine salts have also effects on both the kinetic and the dynamic coagulability, even though the effects are not as intensive as those obtained with associations in which sodium thiosulphate is replaced by an equal proportion of magnesium thiosulphate. In all cases, the aforementioned associations have an anti-agglutinating effect which is greater than the sum of the effects on platelets of their constituents; this is accompanied by a hypocoagulant effect.

Preferably, the proportions of metal (preferably magnesium or sodium) thiosulphate and of papaverine in the drug associations according to the invention are of the order of 1 part by weight of papaverine or of a physiologically acceptable salt thereof (advantageously the hydrochloride or citrate) per 5–20, inter alia 10, parts by weight of metal thiosulphate. For example, tablets can be prepared containing 500 mg. of magnesium thiosulphate in association with 50 mg of papaverine. Of course, the drug for oral administration can be presented in any other form in which the constituents of the association are associated either with pharmaceutically acceptable solid excipients or, in the case of drinkable solutions, with pharmaceutically acceptable liquid excipients.

In the case where the associations used contain 1 part by weight of papaverine and 10 parts by weight of magnesium thiosulphate, the daily doses administered are between 0.5 g and 5 g of magnesium thiosulphate, i.e. 0.05 and 0.50 g papaverine (i.e. 1 to 10 of the aforementioned tablets).

Although oral forms of administration are preferred because of their convenience for patients, the association according to the invention may also be administered parenterally or even by perfusion. In the case of parenteral administration, the constituents of the association are dissolved in a physiologically acceptable, injectable sterile liquid solute. In the case of solutions for perfusion, the association is dissolved in physiological serum, inter alia serum containing glucose. The daily doses by either of the two latter methods, when the association in question contains 10 parts by weight of magnesium thiosulphate for each part by weight of papaverine, are advantageously between 1000 and 4000 mg of magnesium thiosulphate, i.e. between 100 and 400 mg of papaverine.

The association according to the invention can also be administered in the form of suppositories in which case the constituents of the association are mixed with suppository excipients such as saturated fatty-acid glycerides, e.g. the substance comprising a mixture of products sold under the names NOVATA BCF and NOVATA E by the Societe Haenkel. These suppositories contain e.g. 1000 mg magnesium thiosulphate and 100 mg papaverine per unit.

Of course, as the preceding shows, the invention is not limited to those applications and embodiments described in detail, but includes all variants.

We claim:

1. A mixture of papaverine or of a physiologically acceptable papaverine salt with a thiosulphate of a physiologically acceptable metal, the two compounds being in respective proportions effective to have an inhibiting effect on hyperadhesion and hyperagglutination on platelets in blood and also have a marked hypocoagulating effect on the kinetic and dynamic coagulability of whole blood.

2. The mixture of claim 1 wherein the metal thiosulphate is magnesium thiosulphate.

3. The mixture of claim 1 wherein the metal thiosulphate is sodium thiosulphate.

4. The mixture of claim 1 wherein the papaverine is papaverine hydrochloride.

5. The mixture of claim 1 wherein the papaverine is papaverine citrate.

6. The mixture of claim 1 wherein the papaverine is papaverine thienyl 2-carboxylate.

7. The mixture of claim 2 which comprises 5 to 20 parts by weight of magnesium thiosulphate for each part by weight of papaverine.

8. The mixture of claim 7 which comprises approximately 10 parts by weight of magnesium thiosulphate for each part by weight of papaverine.

9. A drug composition comprising the mixture of claim 1 in therapeutically effective dosage to have an inhibiting effect on hyperadhesion and hyperagglutination on platelets in blood and also have a marked hypocoagulating effect on the kinetic and dynamic coagulability of whole blood and a pharmaceutically acceptable carrier.

10. A pharmaceutical composition having an inhibiting effect on hyperadhesion and hyperagglutination effect on blood platelets and increasing the hypocoagulating effect on the kinetic and dynamic coagulabilities of whole blood, which comprises the composition of claim 9, in dosage unit between 1000 and 4000 mg of magnesium thiosulphate and between 100 and 400 mg of papaverine, for 10 parts by weight of magnesium thiosulphate for each part by weight of papaverine.

11. The composition of claim 10 wherein the thiosulphate is magnesium or sodium and the papaverine is the hydrochloride, the citrate or thienyl 2-carboxylate.

12. The composition of claim 11 wherein the thiosulphate is magnesium and the papaverine is the hydrochloride, the citrate or thienyl 2-carboxylate.

13. The composition of claim 11 in dosage unit of 0.5 to 5 parts of the thiosulphate and 0.05 to 0.50 parts of papaverine.

14. A drug composition suitable for oral administration comprising the mixture of claim 1 in therapeutically effective dosage in oral administration to have an inhibiting effect on hyperadhesion and hyperagglutination on platelets in blood and also have a marked hypocoagulating effect on the kinetic and dynamic coagulability of whole blood and a pharmaceutically acceptable excipient.

15. A drug composition suitable for rectal administration comprising the mixture of claim 1 in therapeutically effective dosage in rectal administration to have an inhibiting effect on hyperadhesion and hyperagglutination on platelets in blood and also have a marked hypocoagulating effect on the kinetic and dynamic coagulability of whole blood and a pharmaceutically acceptable excipient.

16. An injectable drug solution for parenterally or perfusion administration comprising the mixture of claim 1 dissolved in a sterile injectable solution for administering the composition parenterally or by perfusion, the composition being effective to have an inhibiting effect on hyperadhesion and hyperagglutination on platelets in blood and also have a marked hypocoagulating effect on the kinetic and dynamic coagulability of whole blood.

17. An aqueous solution comprising a mixture of papaverine or a physiologically acceptable salt thereof with a thiosulfate of a physiologically acceptable metal, the two compounds being in respective proportions effective to have an inhibiting effect on hyperadhesion and hyperagglutination on platelets in blood and also have a marked hypocoagulating effect on the kinetic and dynamic coagulability of whole blood.

18. The solution of claim 17 wherein the proportion of papaverine to the thiosulfate is about 1 part to 5 to 20 parts by weight, respectively.

19. A mixture of papaverine with a thiosulphate of a physiologically acceptable metal, the two compounds being in respective proportions effective to have an inhibiting effect on hyperadhesion and hyperagglutination on platelets in blood and also have a marked hypocoagulating effect on the kinetic and dynamic coagulability of whole blood.

20. The method of controlling agglutination agglutination blood platelets and coagulation of blood plasma which comprises treating a patient with a composition comprising the solution defined in claim 17 and a pharmaceutically acceptable carrier in therapeutically effective dosage.

21. The method of claim 20 wherein the administration is oral.

* * * * *